United States Patent
Lee et al.

(10) Patent No.: US 10,941,351 B2
(45) Date of Patent: Mar. 9, 2021

(54) LAYER-SEPARATION METHOD OF SPENT CAUSTIC SOLUTION

(71) Applicants: SK Innovation Co., Ltd., Seoul (KR); SK Incheon Petrochem Co., Ltd., Incheon (KR)

(72) Inventors: Sung Ho Lee, Incheon (KR); Dong Hyun Kim, Daejeon (KR); Jae Yang Song, Daejeon (KR); Joong Min Park, Daejeon (KR); Sung Wook Jun, Incheon (KR)

(73) Assignees: SK Innovation Co., Ltd., Seoul (KR); SK Incheon Petrochem Co., Ltd., Incheon (KR)

( * ) Notice: Subject to any disclaimer, the term of this patent is extended or adjusted under 35 U.S.C. 154(b) by 309 days.

(21) Appl. No.: 15/796,941

(22) Filed: Oct. 30, 2017

(65) Prior Publication Data

US 2018/0119025 A1    May 3, 2018

(30) Foreign Application Priority Data

Oct. 31, 2016 (KR) .................. 10-2016-0143336

(51) Int. Cl.

| | |
|---|---|
| C10G 19/08 | (2006.01) |
| B01D 11/04 | (2006.01) |
| B01D 17/04 | (2006.01) |
| C07C 31/125 | (2006.01) |
| C07C 69/14 | (2006.01) |
| C07C 69/24 | (2006.01) |
| C10G 33/04 | (2006.01) |

(52) U.S. Cl.
CPC .............. *C10G 19/08* (2013.01); *B01D 11/04* (2013.01); *B01D 11/0488* (2013.01); *B01D 11/0492* (2013.01); *B01D 17/047* (2013.01); *C07C 31/125* (2013.01); *C07C 69/14* (2013.01); *C07C 69/24* (2013.01); *C10G 33/04* (2013.01); *C10G 2300/202* (2013.01); *C10G 2300/4081* (2013.01)

(58) Field of Classification Search
CPC ..................................................... C01G 19/08
See application file for complete search history.

(56) References Cited

U.S. PATENT DOCUMENTS

| | | | |
|---|---|---|---|
| 9,029,624 B2 | 5/2015 | Song et al. | |
| 2014/0140906 A1* | 5/2014 | Song ................. | C01D 1/36 423/183 |
| 2014/0202927 A1* | 7/2014 | Tao .................. | B01D 17/047 208/188 |
| 2016/0326443 A1* | 11/2016 | Young ............... | C10G 33/04 |

FOREIGN PATENT DOCUMENTS

| | | |
|---|---|---|
| JP | 8168605 A | 7/1996 |
| KR | 1020110002233 A | 1/2011 |
| KR | 20130002919 A | 1/2013 |

* cited by examiner

*Primary Examiner* — Peter Keyworth
(74) *Attorney, Agent, or Firm* — The Webb Law Firm

(57) ABSTRACT

Provided are a layer-separation method of a spent caustic solution, and a recycling method of an additive, and more particularly, a layer-separation method of a spent caustic solution including: injecting an additive and an acidic compound to the spent caustic solution occurring from a refinery process to break down a red oil emulsion and to perform layer-separation into an upper layer fraction and a lower layer fraction, wherein the additive is an aliphatic hydrocarbon compound having a water solubility of 0.1 to 10 g/L at 20° C.

7 Claims, 4 Drawing Sheets

LAYER-SEPARATION METHOD OF SPENT CAUSTIC SOLUTION

CROSS-REFERENCE TO RELATED APPLICATION

This application claims priority to Korean Patent Application No. 10-2016-0143336 filed Oct. 31, 2016, the disclosure of which is hereby incorporated in its entirety by reference.

TECHNICAL FIELD

The following disclosure relates to a layer-separation method of a spent caustic solution, and a recycling method of an additive, and more particularly, to a method of improving a separation efficiency between a red oil and the spent caustic solution.

BACKGROUND

In general, products produced from refinery processes and petrochemical processes contain impurities such as hydrogen sulfides, mercaptans, and organic acids, etc. Accordingly, the products are treated with caustic soda (NaOH) or are subjected to scrubbing to thereby remove the impurities.

The caustic soda is a representative strong base, exists as a white translucent crystal, has deliquescence that absorbs moisture in the air, and is used in a form of an aqueous solution in which it is dissolved in water. In particular, the caustic soda has been continuously used as a primary reactant for impurity removal since it is safe, economical, and effective in removing impurities.

However, the caustic soda used to remove impurities is converted to a spent caustic, which is harmful to the human body, and thus, should be treated appropriately. A spent caustic solution has an extremely strong basicity, and has a remarkably high biochemical oxygen demand (BOD), chemical oxygen demand (COD), and total organic carbon (TOC), etc., and thus, it is difficult to be treated by conventional direct biological wastewater treatment methods.

Several methods have been proposed to treat the spent caustic. Among them, incineration may be exemplified as a relatively widely used manner, wherein fuel oil or the like is burned to evaporate liquid components of a waste solution, thereby producing carbon dioxide, alkali metal carbonate, etc., and harmful components are removed from processing facilities such as an incinerator, etc., and discharged to the atmosphere or water system. However, the incineration manner has problems in that an operation cost is high and air pollutants occur during the incineration process.

In addition, there is also known a wet air oxidation method in which an oxygen gas in a micro bubble form is in contact with the spent caustic to perform an oxidation reaction, and then a condensed product is diffused into a bulk liquid to treat the spent caustic. Here, organic materials are converted to carbon dioxide and water, and an inorganic material, sulfide, is converted to thiosulfate or sulfate. However, the wet air oxidation method is generally composed of a preheating apparatus, an oxidation reactor, a cooling apparatus, and a separating apparatus, and thus, a high investment cost is an obstacle (Korean Patent Laid-Open Publication No. 10-2011-0002233).

In addition, in the case of compounds such as a cresol-based compound and a naphthenic acid-based compound, etc., which are the acidic oil components in the spent caustic discharged from a refinery process and/or a petrochemical process, reaction conditions such as temperature and pressure, etc., are required to be precisely adjusted in treatment by the wet air oxidation process, and in particular, high temperature and/or high pressure reaction conditions should be formed depending on properties, which may result in an increase in cost.

Recently, in refinery process and petrochemical process plants, it is necessary to more strictly control liquid or gaseous effluent that may cause air pollution or water pollution. Further, since the spent caustic is a material which is difficult to treat because of high BOD and COD, U. S. Resources Conservation and Recovery Act (RCRA) defines the spent caustic as D003 (reactive sulfide).

As described above, the spent caustic needs to be properly treated to comply with plant emission standards, and appropriate treatment methods need to be used in consideration of types or properties of the spent caustic.

In particular, when phenol-based component and the naphthalic acid-based component, which are known to be high-risk carcinogens in the spent caustic, are relatively highly present, more careful attention is required, and thus, it is necessary to develop a technology capable of separating the components with high efficiency.

RELATED ART DOCUMENT (Patent Document 1) Korean Patent Laid-Open Publication No. 10-2011-0002233 (Jan. 7, 2011)

SUMMARY

An embodiment of the present invention is directed to providing a layer-separation method of a spent caustic solution capable of improving a separation efficiency between a red oil and the spent caustic solution by breaking down an emulsion formed by the red oil, and a recycling method of an additive used for improving the layer-separation efficiency.

In one general aspect, a layer-separation method of a spent caustic solution includes: injecting an additive and an acidic compound to the spent caustic solution occurring from a refinery process to break down a red oil emulsion and to perform layer-separation into an upper layer fraction and a lower layer fraction, wherein the additive is an aliphatic hydrocarbon compound having a water solubility of 0.1 to 10 g/L at 20° C.

In another general aspect, a recycling method of an additive includes: injecting an additive and an acidic compound to a spent caustic solution occurring from a refinery process to break down a red oil emulsion and to perform layer-separation into an upper layer fraction and a lower layer fraction, thereby collecting the upper layer fraction and the lower layer fraction, respectively; regenerating the additive by adding an aqueous caustic solution to the collected upper layer fraction; and re-injecting the regenerated additive into a second spent caustic solution; wherein the additive is an aliphatic hydrocarbon compound having a water solubility of 0.1 to 10 g/L at 20° C.

DETAILED DESCRIPTION OF EMBODIMENTS

Figure 1:
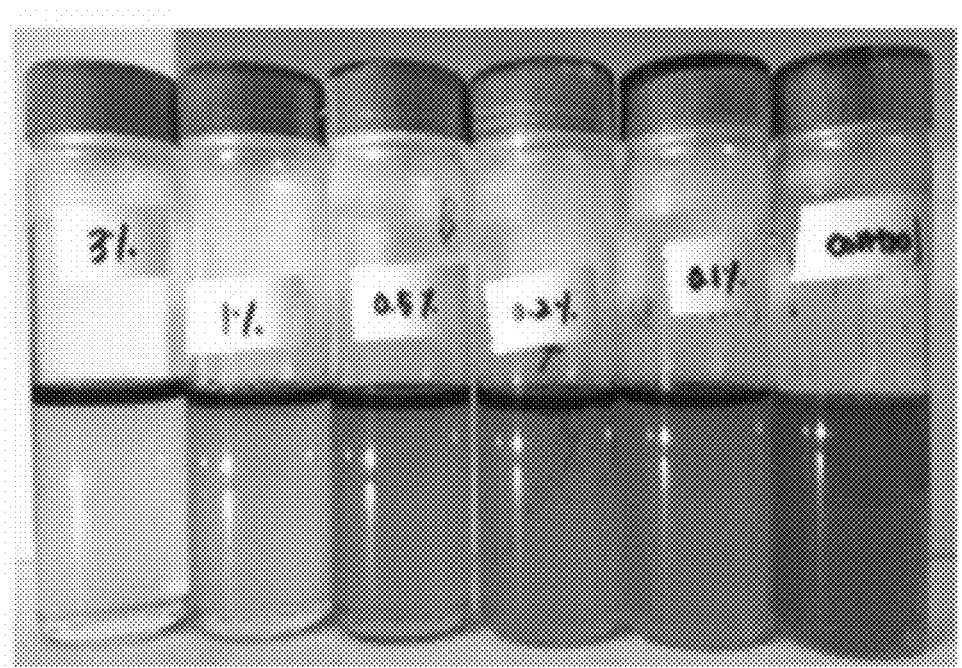
FIG. 1 shows layer-separation efficiencies by varying injection amounts of n-octanol according to an exemplary embodiment of the present invention.
Figure 2:
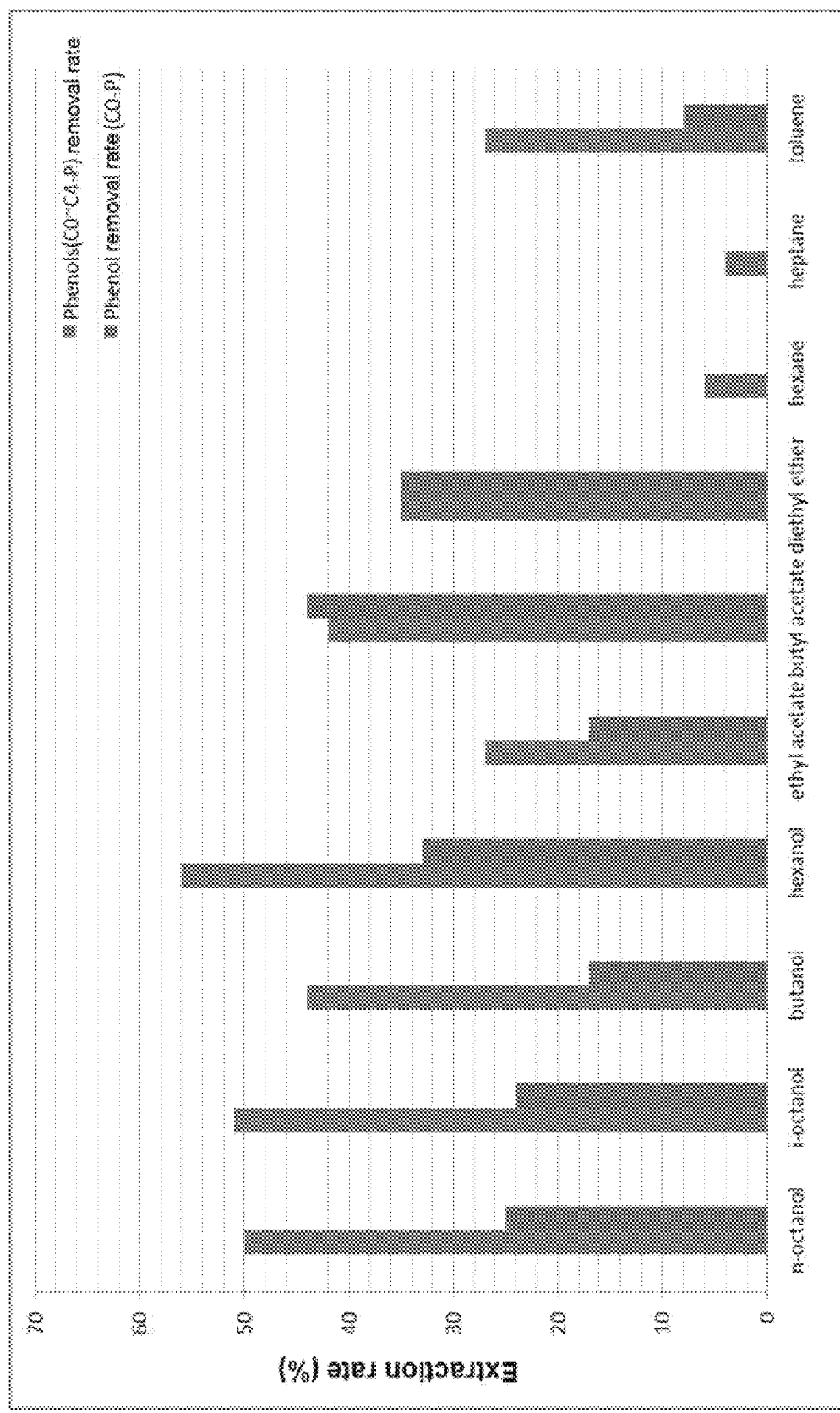
FIG. 2 is a graph showing phenol extraction rates (%) of Examples 1 to 4 and Comparative Examples 2 to 6.
Figure 3:
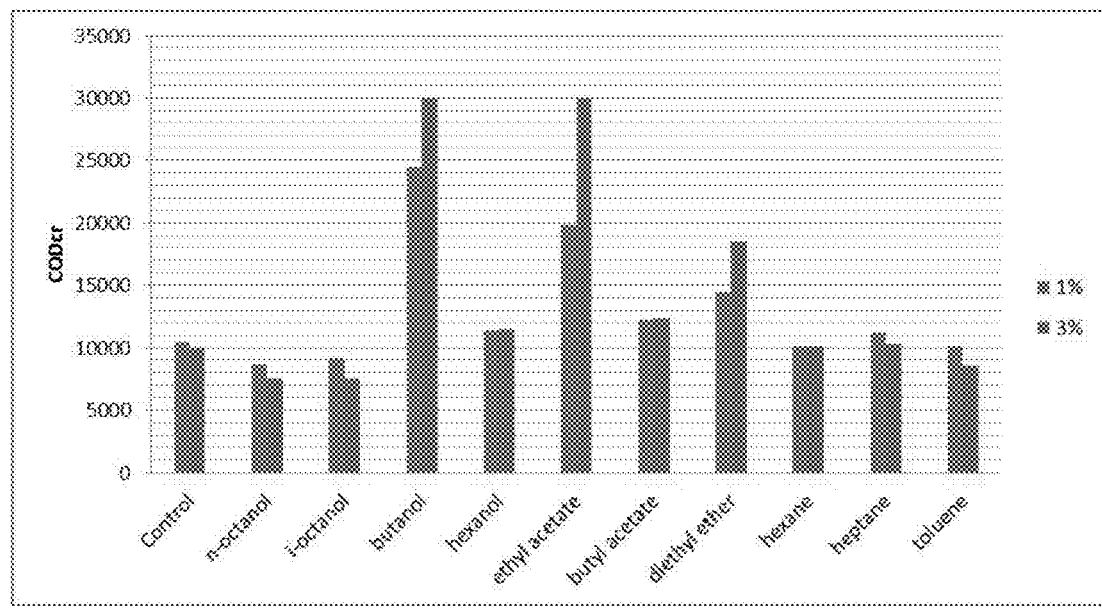
FIG. 3 is a graph showing $COD_{Cr}$ (ppm) of Examples 1 to 4 and Comparative Examples 2 to 6.

Hereinafter, a layer-separation method of a spent caustic solution, and a recycling method of an additive according to the present invention are described in detail with reference to the accompanying drawings. The exemplary embodiments of the present invention to be described below are provided by way of example so that the idea of the present invention can be sufficiently transferred to those skilled in the art to which the present invention pertains. Therefore, the present invention may be implemented in many different forms, without being limited to the drawings to be described below. The drawings may be exaggerated in order to specify the spirit of the present invention. Like reference numerals denote like elements throughout the specification.

Here, unless technical and scientific terms used herein are defined otherwise, they have meanings understood by those skilled in the art to which the present invention pertains. Known functions and components will be omitted so as not to obscure the gist of the present invention in descriptions below and the accompanying drawings.

Meanwhile, in the present invention, a 'red oil' means a mixture including any one or two or more selected from a phenol-based compound, a naphthenic acid-based compound, etc., and may refer to a mixture of reaction by-products generated from a Merox process of a refinery process.

In the present invention, the term 'chemical oxygen demand (COD)' is a value obtained by converting an amount of an oxidant required to chemically decompose and oxidize contaminants in water using a chemical oxidant such as $KMnO_4$, $K_2Cr_2O_7$, or the like, into an amount of oxygen.

In the present invention, the term 'biochemical oxygen demand (BOD)' represents an amount of oxygen consumed when organic materials in water are decomposed and oxidized by aerobic microorganisms, and is generally expressed in units of ppm and mg/L. As the BOD is high, the contamination level in the wastewater is high.

In the present invention, the 'phenol-based compound' means that phenol or a hydrogen group of phenol is substituted with at least one substituent, wherein the substituent may be an alkyl group having 1 to 20 carbon atoms, an alkenyl group having 2 to 20 carbon atoms, an alkynyl group having 2 to 20 carbon atoms, a halogen group, a cyano group, an alkoxy group having 1 to 20 carbon atoms, an alkylthio group having 1 to 20 carbon atoms, an alkylcarbonyl group having 1 to 20 carbon atoms, an alkenylcarbonyl group having 1 to 20 carbon atoms, etc. As a more specific example, the phenol-based compound may be phenol, cresol, dimethyl phenol, or the like, but is not limited thereto.

In the present invention, the 'naphthenic acid-based compound' is a kind of carboxylic acid, for example, R—COOH, wherein R may be a cyclic alkyl having 5 to 6 carbon atoms or a derivative thereof. More specifically, the 'naphthenic acid-based compound' may be represented by Chemical Formula below:

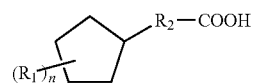

[Chemical Formula]

in Chemical Formula, $R_1$ is an alkyl group having 1 to 20 carbon atoms, $R_2$ is an alkylene group having 1 to 20 carbon atoms, and n is an integer of 1 to 4.

The spent caustic solution in the present invention occurs from a kero merox process of a refinery process, and specifically, for example, may occur from caustic soda used to remove $H_2S$ and naphthenic acid from kerosene.

As a source of the above-described spent caustic solution, for example, in a merox process of the refining process, a spent caustic solution may be formed by reactions with the caustic soda as shown in the following Reaction Schemes 1 to 3, etc.:

[Reaction Scheme 1]

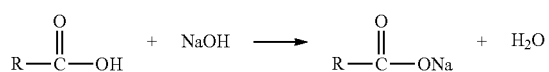

[Reaction Scheme 2]

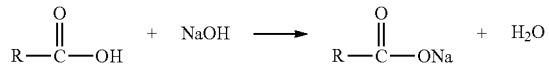

[Reaction Scheme 3]

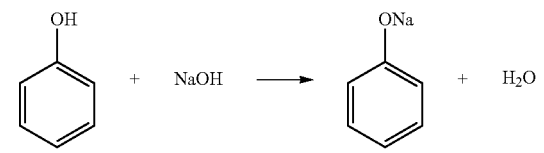

The thus-prepared spent caustic solution has a very strong alkaline property having a pH of about pH 12 to 14, and in particular, the spent caustic solution occurring from the refinery process has a high COD level, and in some cases, the high COD level may be about 65,000 mg/L or more, and more specifically about 70,000 to 90,000 mg/L. In addition, a concentration of phenol in the spent caustic solution may typically be about 2,000 to 40,000 mg/L, and more specifically about 2,000 to 8,000 mg/L.

As described above, since the spent caustic solution has a very strong alkaline property, and thus, a pH adjusting process to which an acid is added may be used to lower the pH, and thus, an upper layer fraction and a lower layer fraction may be separated. The upper layer fraction separated and collected by the layer-separation method is a kind of reaction by-product, and may include any one or two or more compounds selected from a phenol-based compound, a naphthenic acid-based compound, etc. The upper layer fraction is referred to as 'red oil' since it is viscous and brown. The red oil component may vary in properties depending on the type of spent caustic, but may include about 20 to 30 wt % of light components having a boiling point of about 230° C. or lower and about 70 to 80 wt % of heavy components having a boiling point higher than about 230° C. The above numerical ranges are illustrative, and the present invention is not limited thereto.

Most of the light components are phenol-based compounds such as phenol, cresol, dimethylphenol, etc., but most of the heavy components are a mixture of naphthenic acid-based compounds and may have a molecular weight (Mw) of about 200 to 400 g/mol. Further, gaseous components produced during a neutralization process, such as hydrogen sulfide, are discharged to the outside of the reactor and removed.

The reason for separating the red oil as described above is that the oil component may be coated on the catalyst in a subsequent oxidation treatment process, which may interfere with smooth oxidation reaction and fluid flow in the catalyst, and a large amount of hydrogen peroxide must be used for the subsequent oxidation treatment, which may cause an increase in the operation cost and may cause operating difficulties. Besides, since residual organic components act as toxic materials in the subsequent treatment process, for example, a biological treatment process in the future, and thus, there is a need to remove these residual organic components to a certain level prior to the oxidation treatment.

However, when using only the conventional method of treating the spent caustic solution with an acid, the red oil easily forms an emulsion and the formed red oil emulsion is dispersed throughout the entire spent caustic solution as shown in the control group of FIG. 1, and thus, there is a disadvantage in that the layer-separation efficiency and a removal efficiency thereof are greatly reduced.

Accordingly, the present inventors attempted to improve a process efficiency in treating the spent caustic by injecting an additive satisfying a specific condition into a pH-adjusted spent caustic solution to thereby break down the emulsion formed by the red oil and improve a layer-separation efficiency of the upper layer fraction and the lower layer fraction.

In detail, a layer-separation method of a spent caustic solution according to an exemplary embodiment of the present invention may include injecting an additive and an acidic compound to the spent caustic solution occurring from a refinery process to break down a red oil emulsion and to perform layer-separation into an upper layer fraction and a lower layer fraction, wherein the additive may be an aliphatic hydrocarbon compound having a water solubility of 0.1 to 10 g/L at 20° C.

Here, the red oil emulsion may be formed by a compound including any one or two or more selected from a phenol-based compound and a naphthenic acid-based compound.

As described above, by injecting the additive that satisfies the specific condition into the pH-adjusted spent caustic solution to break down the emulsion formed by the red oil and to promote phase separation, a layer-separation efficiency of the upper layer fraction and the lower layer fraction may be improved as shown in FIG. 1. That is, it is possible to improve the layer-separation efficiency of the spent caustic solution which is the lower layer fraction and the red oil which is the upper layer fraction, and thus, as the red oil is completely layer-separated, a removal amount of the red oil relative to the spent caustic solution only treated with acid may be significantly increased.

Hereinafter, the present invention will be described in detail.

First, a step of injecting an additive and an acidic compound to a spent caustic solution occurring from a refinery process may be performed. The acidic compound may be injected into the spent caustic solution to adjust pH of the spent caustic solution, and further, the additive may be added to break down the emulsion formed from the red oil in the spent caustic solution. Here, an injection order of the additive and the acidic compound is not particularly limited, and any one of the two may be injected first, or both may be injected at the same time.

In one example of the present invention, the acidic compound may be injected through the same method as the pH adjustment step of the spent caustic solution. For example, even though the present invention does not preclude the use of other acid components, it may be desirable to appropriately select the kind of acid in consideration of difficulties in selecting the material of the reactor due to corrosion by acid, etc. In this viewpoint, it may be preferable to use sulfuric acid as the acidic compound. Further, the acidic compound to be added may be a sulfuric acid stock solution having a concentration of 98 vol %, but in some cases, a diluted aqueous solution form may also be used.

The added amount of the acidic compound may vary depending on pH of the spent caustic solution. For example, the acid may be added until pH of the spent caustic solution is 1 to 5. That is, the spent caustic solution may be adjusted to have a pH of 1 to 5 by injecting an acidic compound thereinto. In this range, the layer-separation efficiency according to the addition of the additive may be more excellent.

In one example of the present invention, it is preferable to select the additive that may break down the emulsion formed by the red oil, has a low water solubility and a high selectivity to red oil, and has no reaction with sulfuric acid and sodium hydroxide.

Specifically, as mentioned above, the additive according to an exemplary embodiment of the present invention may have a water solubility of 0.1 to 10 g/L at 20° C. As described above, the water solubility is very low, which effectively breaks down the red oil emulsion and improves the layer-separation efficiency of the spent caustic solution, and at the same time, it is not dissolved well in water, and thus, the COD may be reduced. More preferably, the water solubility at 20° C. may be 0.2 to 5 g/L, and more preferably from 0.3 to 2 g/L. By satisfying this condition, the removal efficiency of the red oil may be greatly improved, and the COD may be greatly reduced.

Further, the additive may be an aliphatic hydrocarbon compound. The aliphatic hydrocarbon compound may satisfy the water solubility of 0.1 to 10 g/L at 20° C., but when an aromatic hydrocarbon compound or an alicyclic hydrocarbon compound is used as an additive, it has a similar structure to the phenol-based compound or the naphthenic acid-based compound, and thus, the formation of the red oil emulsion may be rather promoted, and the layer-separation efficiency may be lowered.

As a preferred example of the additive, the aliphatic hydrocarbon compound may be an aliphatic alcohol compound having 8 to 10 carbon atoms or an aliphatic ester compound having 6 to carbon atoms, or the like. These compounds are preferable since the water solubility at 20° C. satisfies 0.1 to 10 g/L, selectivity to the red oil is high, and there is no reaction with sulfuric acid and sodium hydroxide.

As a more specific example, the aliphatic alcohol compound may be any one or two or more selected from 1-octanol, and 2-ethyl-1-hexanol, and the aliphatic ester compound may be any one or two or more selected from butyl acetate, pentyl acetate, hexyl acetate, and propyl propionate, but the aliphatic alcohol compound and the aliphatic ester compound are not necessarily limited thereto. In particular, preferably, the additive may be 2-ethyl-1-hexanol since 2-ethyl-1-hexanol is advantageous to have an effect of breaking down the red oil emulsion and a very excellent layer-separation efficiency accordingly, and thus, the red oil in the spent caustic solution may be removed as much as possible, and at the same time, the COD reduction effect may be excellent to improve a process efficiency of treating the spent caustic solution.

It is preferable to adjust an added amount of the additive according to the amount of the spent caustic solution. Specifically, for example, the additive may be added in an amount of 0.1 to 20 vol % in the spent caustic solution. That is, a volume ratio of the spent caustic solution to the additive may be 99.9 to 80:0.1 to 20. In this range, the effect of breaking down the red oil emulsion may be excellent to improve the layer-separation efficiency.

More preferably, the volume ratio of the spent caustic solution and the additive may be 99.5 to 90:0.5 to 10, and more preferably 97 to 90:3 to 10. In such a range, the red oil emulsion in the lower layer fraction may be almost completely broken, and thus, the layer-separation efficiency may be greatly improved, and waste caused by addition of an excessive amount of the additive may be prevented.

After the layer-separation, each of the upper layer fraction and the lower layer fraction may be collected or removed by conventional methods. For example, pipes and valves may be provided on both sides of the bottom of a reactor, the spent caustic solution, which is the lower layer fraction that occupies a relatively large space may be discharged first, and the remaining upper layer fraction, that is, the red oil, may be discharged and collected by other pipes.

Here, the collected upper layer fraction includes an additive in addition to the red oil, and the additive may be regenerated and recirculated to the layer-separation process, thereby being recycled.

Specifically, the recycling method of an additive according to an exemplary embodiment of the present invention may include: injecting an additive and an acidic compound to a spent caustic solution occurring from a refinery process to break down a red oil emulsion and to perform layer-separation into an upper layer fraction and a lower layer fraction, thereby collecting the upper layer fraction and the lower layer fraction, respectively; regenerating the additive by adding an aqueous caustic solution to the collected upper layer fraction; and re-injecting the regenerated additive into a second spent caustic solution; wherein the additive is an aliphatic hydrocarbon compound having a water solubility of 0.1 to 10 g/L at 20° C.

Here, the layer-separation method of the upper layer fraction and the lower layer fraction and the collecting method thereof are the same as those described above, and overlapped descriptions will be omitted.

The upper layer fraction and the lower layer fraction may be collected, respectively, and then, the step of regenerating the additive by adding an aqueous caustic solution to the collected upper layer fraction may be performed. The step is a layer-separation step of the red oil and the additive by dissolving the red oil included in the upper layer fraction into the aqueous solution through reaction with the caustic soda again, wherein the red oil and the additive that are layer-separated may be separated and collected, respectively, through conventional methods.

Here, it is preferable to add the aqueous caustic solution to such an extent that the red oil is capable of being sufficiently dissolved. For example, 20 to 60 vol % of the aqueous caustic solution may be added to 100 vol % of the red oil, based on a concentration of 25 wt % of the aqueous caustic solution. In this range, the red oil may be effectively dissolved in the aqueous caustic solution and may be well separated from the additive. More preferably, the aqueous caustic solution may be added in an amount of 40 to 60 vol %, and more preferably, 50 to 60 vol %, based on 100 vol % of the red oil. Provided that the added amount of the aqueous caustic solution is determined based on the concentration of 25 wt %, and thus, it is needless to say that, when the concentration of the aqueous caustic solution is changed, the added amount may be adjusted. In a specific example, the concentration of the aqueous caustic solution may be 20 to 50 wt %.

Next, a step of re-injecting the regenerated additive into a second spent caustic solution may be performed. Here, the regenerated additive may mean an additive separated from the red oil by adding the aqueous caustic solution to the upper layer fraction.

Figure 5:
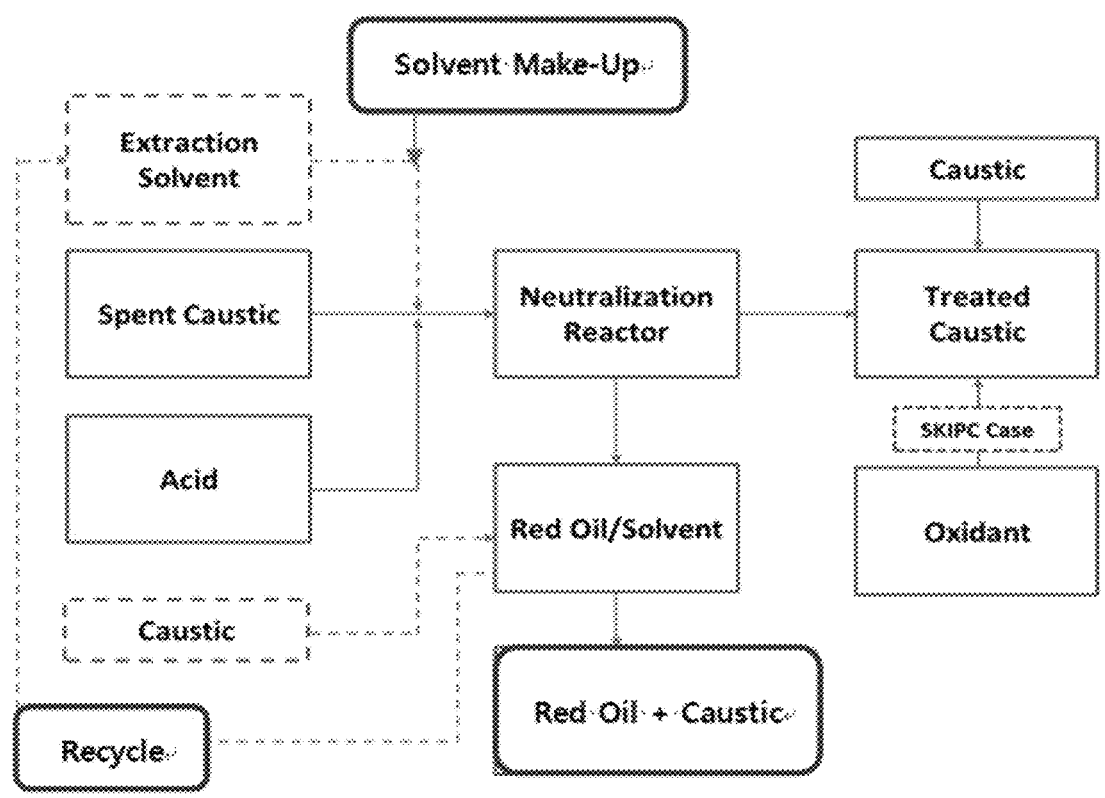
FIG. 5 is a process chart showing treatment of a spent caustic solution, wherein the solid lines are existing treatment processes of the spent caustic, and the dotted lines are treatment processes that are added for improving the layer-separation efficiency according to an exemplary embodiment of the present invention.

This step is a step of recycling the regenerated additive. As shown in FIG. 5, the additive that is injected into the first spent caustic solution may be regenerated and may be re-injected into another spent caustic solution, that is, the second spent caustic solution, thereby recycling the additive, and thus, it is possible to improve a process operation efficiency and to reduce the operation cost.

Hereinafter, a layer-separation method of a spent caustic solution, and a recycling method of an additive according to the present invention are described in more detail with reference to Examples. Meanwhile, the following exemplary embodiments and examples are provided as a reference for explaining the present invention in detail, and therefore, the present invention is not limited thereto, but may be implemented in various ways.

Unless defined otherwise, all technical and scientific terms used herein have the same meanings generally understood by those skilled in the art to which the present disclosure pertains. Terms used in the specification of the present invention are to effectively describe specific exemplary embodiments, but are not intended to limit the present invention.

In addition, additives are used in unit of wt % unless specifically described in the specification.

[Measurement of Physical Properties]

1) Phenol extraction rate (%)=$((P_{SC}-PT_{SC})/P_{SC})\times100$ ($P_{SC}$ is an amount of phenols (ppm) in an initial spent caustic solution, and $PT_{TSC}$ is an amount of phenols (ppm) in a final spent caustic solution after treating the initial spent caustic solution with the sulfuric acid and the additive to separate the red oil). Here, the phenols are phenol (C0-P), cresol (C1-P), dimethylphenol (C2-P), trimethylphenol (C3-P) and tetramethylphenol (C4-P).

2) Measurement of $COD_{Cr}$ (ppm): $K_2Cr_2O_7$ was used as a chemical oxidant, and an amount of oxidant required to chemically decompose and oxidize the spent caustic from which the red oil was separated was measured, and analyzed by using a COD kit.

Example 1

A sulfuric acid aqueous solution having a concentration of 98 vol % was added to the spent caustic solution occurring from the refinery process to adjust an acidity to about pH 2. Here, an amount (ppm) of phenols in the spent caustic solution was 1,420 ppm.

Next, the pH-adjusted spent caustic solution and n-octanol were mixed so that a volume ratio of the pH-adjusted spent caustic solution to n-octanol was 99:1, and subjected to layer-separation.

Example 2

The pH-adjusted spent caustic solution which was the same as in Example 1 was used, and all procedures were performed in the same manner as in Example 1 except that 2-ethyl-1-hexanol was used instead of n-octanol as an additive.

Example 3

The pH-adjusted spent caustic solution which was the same as in Example 1 was used, and all procedures were performed in the same manner as in Example 1 except that n-hexanol was used instead of n-octanol as an additive.

Example 4

The pH-adjusted spent caustic solution which was the same as in Example 1 was used, and all procedures were performed in the same manner as in Example 1 except that butyl acetate was used instead of n-octanol as an additive.

Comparative Example 1

A sulfuric acid aqueous solution having a concentration of 98 vol % was added to the spent caustic solution occurring from the refinery process to adjust an acidity to pH 2, and the obtained mixture was subjected to layer-separation.

Comparative Example 2

The pH-adjusted spent caustic solution which was the same as in Example 1 was used, all procedures were performed in the same manner as in Example 1 except that n-butanol was used instead of n-octanol as an additive.

Comparative Example 3

The pH-adjusted spent caustic solution which was the same as in Example 1 was used, and all procedures were performed in the same manner as in Example 1, except that ethyl acetate was used instead of n-octanol as an additive.

Comparative Example 4

The pH-adjusted spent caustic solution which was the same as in Example 1 was used, and all procedures were performed in the same manner as in Example 1, except that n-heptane was used instead of n-octanol as an additive.

Comparative Example 5

The pH-adjusted spent caustic solution which was the same as in Example 1 was used, and all procedures were performed in the same manner as in Example 1, except that n-hexane was used instead of n-octanol as an additive.

Comparative Example 6

The pH-adjusted spent caustic solution which was the same as in Example 1 was used, and all procedures were performed in the same manner as in Example 1, except that toluene was used instead of n-octanol as an additive.

TABLE 1

| | Additive | Water solubility (g/L) | $P_{SC}$ (ppm) | $P_{TSC}$ (ppm) | Phenol extraction rate (%) | $COD_{Cr}$ (ppm) |
|---|---|---|---|---|---|---|
| Example 1 | n-Octanol | 0.46 (at 25° C.) | 1,420 | 710 | 50.0 | 8,678 |
| Example 2 | 2-Ethyl-1-hexanol | 1.0 (at 20° C.) | | 700 | 50.7 | 9,162 |
| Example 3 | n-Hexanol | 5.9 (at 20° C.) | | 630 | 55.6 | 11,360 |
| Example 4 | Butyl acetate | 6.8 (at 20° C.) | | 540 | 62.0 | 12,249 |
| Comparative Example 1 | — | — | | 940 | 33.8 | 10,475 |
| Comparative Example 2 | n-Butanol | 73 (at 25° C.) | | 790 | 44.4 | 24,522 |
| Comparative Example 3 | Ethyl acetate | 83 (at 20° C.) | | 1,040 | 26.7 | 19,873 |
| Comparative Example 4 | n-Heptane | 0.003 (at 20° C.) | | 1,360 | 4.2 | 11,185 |
| Comparative Example 5 | n-Hexane | 0.0095 (at 25° C.) | | 1,330 | 6.3 | 10,134 |
| Comparative Example 6 | Toluene | 0.52 (at 20° C.) | | 1,030 | 27.5 | 10,136 |

As shown in Table 1, in Examples 1 to 4 in which the additive having water solubility satisfying 0.1 to 10 g/L at 20° C. according to the present invention was added, it could be confirmed that a phenol extraction rate was excellent as 50% or more, and thus, the red oil emulsion was broken to greatly improve a layer-separation efficiency, and it could be confirmed that $COD_{Cr}$ was measured to be less than 12,500 ppm, and thus, a COD reduction efficiency was excellent.

In particular, in Example 2, it could be confirmed that the phenol extraction rate was measured to be about 51%, the $COD_{Cr}$ was measured to be less than 10,000 ppm, and the layer-separation efficiency and the COD reduction efficiency were both excellent, and thus, 2-ethyl-1-hexanol could be used as the most preferable additive.

On the other hand, in Comparative Example 1 in which the additive was not added, as shown in the control group of FIG. 1, the layer-separation efficiency was poor due to the emulsion formed by the red oil, and thus, the phenol extraction rate was reduced to be about 34%.

In Comparative Example 2, the solubility to phenols was excellent, and the phenol extraction rate was not significantly different from that in Example 1, but $COD_{Cr}$ was measured to be very high as about 24,500 ppm due to high water solubility.

In Comparative Example 3, since the solubility to phenols was low, the effect of breaking down the red oil emulsion was low, and thus, the phenol extraction rate was significantly reduced to be about 27%. Further, due to the high water solubility, $COD_{Cr}$ was measured to be significantly high as about 20,000 ppm.

In Comparative Examples 4 and 5, the solubility to phenols was remarkably low, and thus, the phenol extraction rate was remarkably low, i.e., less than 10%.

In Comparative Example 6, the solubility to phenols was excellent, but the effect of breaking down the red oil emulsion was poor due to the structure similar to phenols. As a result, the layer-separation efficiency was greatly reduced, and the phenol extraction rate was greatly reduced to be about 27%.

Example 5

The pH-adjusted spent caustic solution which was the same as in Example 1 was used, and all procedures were performed in the same manner as in Example 1, except that the pH-adjusted spent caustic solution and n-octanol were mixed so that the volume ratio of the pH-adjusted spent caustic solution to n-octanol was 99.9:0.1.

Example 6

The pH-adjusted spent caustic solution which was the same as in Example 1 was used, and all procedures were performed in the same manner as in Example 1, except that the pH-adjusted spent caustic solution and n-octanol were mixed so that the volume ratio of the pH-adjusted spent caustic solution to n-octanol was 99.8:0.2.

Example 7

The pH-adjusted spent caustic solution which was the same as in Example 1 was used, and all procedures were performed in the same manner as in Example 1, except that the pH-adjusted spent caustic solution and n-octanol were mixed so that the volume ratio of the pH-adjusted spent caustic solution to n-octanol was 99.5:0.5.

Example 8

The pH-adjusted spent caustic solution which was the same as in Example 1 was used, and all procedures were performed in the same manner as in Example 1, except that the pH-adjusted spent caustic solution and n-octanol were mixed so that the volume ratio of the pH-adjusted spent caustic solution to n-octanol was 97:3.

Example 9

The pH-adjusted spent caustic solution which was the same as in Example 1 was used, and all procedures were performed in the same manner as in Example 1, except that the pH-adjusted spent caustic solution and n-octanol were mixed so that the volume ratio of the pH-adjusted spent caustic solution to n-octanol was 95:5.

Example 10

The pH-adjusted spent caustic solution which was the same as in Example 1 was used, and all procedures were performed in the same manner as in Example 1, except that the pH-adjusted spent caustic solution and n-octanol were mixed so that the volume ratio of the pH-adjusted spent caustic solution to n-octanol was 90:10.

TABLE 2

| | Additive | Water solubility (25° C., g/L) | $P_{SC}$ (ppm) | $P_{TSC}$ (ppm) | Phenol extraction rate (%) |
|---|---|---|---|---|---|
| Example 5 | n-Octanol | 0.46 | 1,420 | 1,250 | 12.0 |
| Example 6 | | | | 1,190 | 16.2 |
| Example 7 | | | | 970 | 31.7 |
| Example 8 | | | | 430 | 69.7 |
| Example 9 | | | | 320 | 77.5 |
| Example 10 | | | | 250 | 82.4 |

Figure 4:
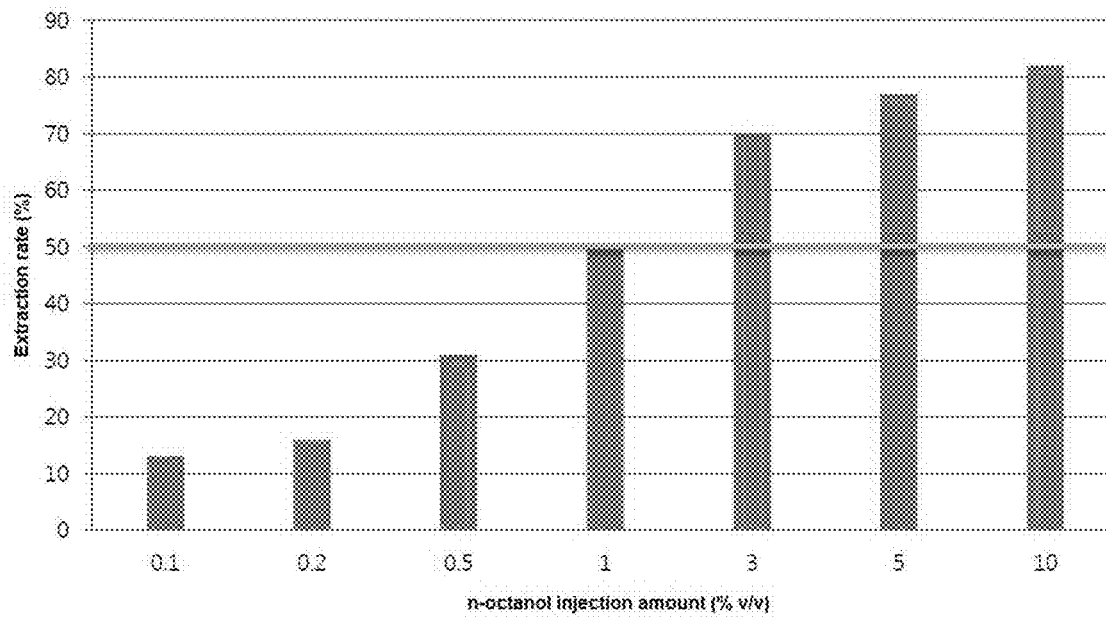
FIG. 4 is a graph showing phenol extraction rates (%) of Example 1 and Examples 5 to 10.

Examples 5 to 10 show the layer-separation efficiency and the phenol efficiency according to the added amount of the additive. As shown in FIGS. 1 and 4, it could be confirmed that when the additive was added in an amount of 1 vol % or more, the effect of breaking down the red oil emulsion was particularly excellent, and the layer-separation efficiency was significantly improved, and thus, as a result, the phenol extraction rate was very excellent as 50% or more.

Example 11

A sulfuric acid aqueous solution having a concentration of 98 vol % was added to the spent caustic solution occurring from the refinery process to adjust an acidity to pH 2.

Next, the pH-adjusted spent caustic solution and n-octanol were mixed so that a volume ratio of the pH-adjusted spent caustic solution to n-octanol was 99:1, and layer-separated.

Next, the upper layer fraction and the lower layer fraction were collected, respectively, and the aqueous caustic solution having a concentration of 25 vol % was added to the upper layer fraction in an amount of 50 vol % relative to the volume of the red oil to separate the red oil and the additive, and the additive was regenerated.

The regenerated additive was re-injected into another spent caustic solution at the same volume ratio as above, and recycled.

The phenol extraction rate was 45%, which was the same as that before recycling, and $COD_{Cr}$ was excellent as about 9,310 ppm.

The layer-separation method of a spent caustic solution according to the present invention may improve the layer-separation efficiency of the upper layer fraction and the lower layer fraction by injecting the additive that satisfies the specific condition into the pH-adjusted spent caustic solution to break down the emulsion formed by the red oil and to promote phase separation. That is, it is possible to improve the layer-separation efficiency of the spent caustic solution which is the lower layer fraction and the red oil which is the upper layer fraction, and thus, as the red oil is completely layer-separated, a removal amount of the red oil relative to the spent caustic solution only treated with acid may be significantly increased.

Further, by using the additive that satisfies the specific condition, COD may be reduced to improve the process efficiency in treating the spent caustic solution.

Hereinabove, although the present invention is described by specific matters and limited exemplary embodiments, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the claims to be described below as well as all modified equally or equivalently to the claims are intended to fall within the scopes and spirit of the present invention.

What is claimed is:

1. A layer-separation method of a spent caustic solution comprising:
    injecting an additive and an acidic compound to the spent caustic solution occurring from a refinery process to break down a red oil emulsion and to perform layer-separation into an upper layer fraction and a lower layer fraction; and
    regenerating the additive by adding an aqueous caustic solution to the upper layer fraction,
    wherein the additive has a water solubility of 0.1 to 10 g/L at 20° C. and is any one or two or more selected from n-octanol, n-hexanol, and an aliphatic ester compound having 6 to 10 carbon atoms.

2. The layer-separation method of claim 1, wherein the aliphatic ester compound is any one or two or more selected from butyl acetate, pentyl acetate, hexyl acetate, and propyl propionate.

3. The layer-separation method of claim 1, wherein a volume ratio of the spent caustic solution to the additive is 99.9 to 80:0.1 to 20.

4. The layer-separation method of claim 1, wherein the spent caustic solution is adjusted to have a pH of 1 to 5 by injecting an acidic compound.

5. The layer-separation method of claim 1, wherein the red oil emulsion is formed by a compound including any one or two or more selected from a phenol-based compound and a naphthenic acid-based compound.

6. The layer-separation method of claim 1, wherein the additive has a water solubility of 0.1 to 10 g/L at 20° C. and is an aliphatic ester compound having 6 to 10 carbon atoms.

7. A recycling method of an additive comprising:
    injecting an additive and an acidic compound to a spent caustic solution occurring from a refinery process to break down a red oil emulsion and to perform layer-separation into an upper layer fraction and a lower layer fraction, thereby collecting the upper layer fraction and the lower layer fraction, respectively;
    regenerating the additive by adding an aqueous caustic solution to the collected upper layer fraction; and
    re-injecting the regenerated additive into a second spent caustic solution;
    wherein the additive is an aliphatic hydrocarbon compound having a water solubility of 0.1 to 10 g/L at 20° C.

* * * * *